(12) United States Patent
Woods et al.

(10) Patent No.: US 7,149,633 B2
(45) Date of Patent: Dec. 12, 2006

(54) DISPLACEMENT METHOD OF KNOT SIZING

(75) Inventors: Steve Woods, Salmon Arm (CA); Ron Lahoda, Salmon Arm (CA); Jacek M. Biernacki, Salmon Arm (CA); Carl Flatman, Salmon Arm (CA)

(73) Assignee: Coe Newnes/McGettee Inc., Salmon Arm (CA)

( * ) Notice: Subject to any disclaimer, the term of this patent is extended or adjusted under 35 U.S.C. 154(b) by 20 days.

(21) Appl. No.: 11/061,874

(22) Filed: Feb. 22, 2005

(65) Prior Publication Data

US 2005/0190958 A1    Sep. 1, 2005

Related U.S. Application Data

(60) Provisional application No. 60/547,445, filed on Feb. 26, 2004.

(51) Int. Cl.
    *G01R 27/26* (2006.01)
(52) U.S. Cl. .................. 702/40; 702/42; 324/637; 324/640; 324/667; 324/663; 73/597; 73/598; 34/381; 348/381; 382/141; 144/357
(58) Field of Classification Search ............. None
    See application file for complete search history.

(56) References Cited

U.S. PATENT DOCUMENTS

| | | | |
|---|---|---|---|
| 4,283,629 A * | 8/1981 | Habermehl et al. ............ 378/4 |
| 4,500,835 A * | 2/1985 | Heikkila ..................... 324/631 |
| 4,831,545 A * | 5/1989 | Floyd et al. ................. 702/40 |
| 4,879,752 A * | 11/1989 | Aune et al. ................. 382/141 |
| 4,926,350 A * | 5/1990 | Bechtel et al. ............... 702/36 |
| 4,941,357 A | 7/1990 | Schajer |
| 5,023,805 A * | 6/1991 | Aune et al. ................... 702/38 |
| 5,394,342 A | 2/1995 | Poon |
| 5,585,732 A | 12/1996 | Steele et al. |
| 5,960,104 A * | 9/1999 | Conners et al. ............ 382/141 |
| 6,151,379 A * | 11/2000 | Kullenberg et al. ........... 378/54 |
| 6,157,698 A | 12/2000 | Pietikainen et al. |
| 6,272,437 B1 | 8/2001 | Woods et al. |
| 6,594,590 B1 | 7/2003 | Woods et al. |

(Continued)

FOREIGN PATENT DOCUMENTS

WO    WO 91/05245    4/1991

(Continued)

*Primary Examiner*—Carol S. W. Tsai
(74) *Attorney, Agent, or Firm*—Antony C. Edwards

(57) ABSTRACT

A method of estimating the displaced size of a knot in a lumber piece includes the steps of: translating the lumber piece downstream along a flow path between a radiation source and sensor while simultaneously irradiating the lumber piece with radiation from the first radiation source whereby the radiation is attenuated by the lumber piece; collecting a set of radiation intensity data from the radiation sensor as the lumber piece is irradiated; processing the set of radiation intensity data to sum the radiation intensity data and to provide radiation intensity profiles transversely of the flow path direction and corresponding density profiles transversely of the flow path direction; mapping the density profiles to model a set of three dimensional density profiles of the lumber piece; processing the radiation intensity data to determine a clear wood density threshold value for the lumber piece and a maximum density value of the density profiles; and, computing a ratio of the summed density profile values to the summed maximum density values for the density profiles and multiplying the ratio with the transverse width of the lumber piece.

8 Claims, 5 Drawing Sheets

U.S. PATENT DOCUMENTS

| | | |
|---|---|---|
| 6,756,789 B1 | 6/2004 | Parker et al. |
| 6,757,354 B1* | 6/2004 | Skatter et al. .................. 378/58 |
| 6,784,672 B1 | 8/2004 | Steele et al. |
| 2002/0025061 A1* | 2/2002 | Metcalfe et al. ............ 382/108 |
| 2003/0222658 A1* | 12/2003 | Schajer ....................... 324/639 |
| 2004/0057551 A1* | 3/2004 | Skatter et al. ................. 378/54 |
| 2005/0086023 A1* | 4/2005 | Ziegler et al. .............. 702/127 |
| 2005/0190958 A1* | 9/2005 | Woods et al. ............... 382/141 |

FOREIGN PATENT DOCUMENTS

WO    WO 2004/106918    12/2004

\* cited by examiner

DISPLACEMENT METHOD OF KNOT SIZING

CROSS REFERENCE TO RELATED APPLICATION

This application claims priority from U.S. Provisional Patent Application No. 60/547,445 filed Feb. 26, 2004 entitled Displacement Method of Knot Sizing.

FIELD OF THE INVENTION

This invention relates to a method and apparatus for determining the displaced size of knots in the lumber.

BACKGROUND OF THE INVENTION

In the prior art, applicant is aware of several patents which issued to Aune et al. the particulars of which follow, which teach that it is known to use x-ray radiators and detectors positioned on either side of a piece of lumber for detecting defects in the lumber based on variation of detected density as the lumber is passed between the radiation source and the detector:

In the prior art, applicant is aware of U.S. Pat. No. 4,941,357 which issued to Schajer on Jul. 17, 1990 for a Method for Estimating the Strength of Wood wherein a method is described for measuring the longitudinal density profile of a piece of wood so as to allow estimation of the strength or stiffness of the wood by determining the clear wood and identifying structural defects by sharp density increases caused by knots. Applicant is also aware of U.S. Pat. No. 5,023,805 which issued to Aune et al. on Jun. 11, 1991 for a Log Scanner wherein it is taught to analyze a log containing knots by passing electromagnetic energy through the log and sensing the amount of energy passing through by sensors mounted opposite to the energy source. For asymmetric bodies at least two sources of electromagnetic energy are employed providing then for the longitudinal plans to be analyzed to identify the same different density element in each of the plans and to then reconstruct the log with the detected elements positioned in cross sections of the log. Applicant is also aware of U.S. Pat. No. 4,879,752 which issued to Aune et al. on Nov. 7, 1989 for a Lumber Optimizer wherein a lumber optimizer system is described which detects wane in a flitch by detecting the amount of electromagnetic radiation passing through localized areas of the flitch board to determine local differences in density and thereby a density profile of the flitch. A computer is employed to provide a profile of signal strengths generated by the detectors corresponding to the electromagnetic radiation sources, the computer generating an image of varying intensity depending on the signal, that is density for each discreet area of the flitch and to provide a density map. Defects, including their nature and position are determined from analysis of the map.

Applicant is also aware U.S. Pat. No. 5,394,342 which issued to Poon on Feb. 28, 1995 for an invention entitled Log Scanning. Poon teaches to scan the length of a log to provide a longitudinal density scan. Density peaks are plotted to form an image and adjacent peaks in adjacent rows and columns of pixels in the detectors are joined to provide an image depicting spines of detected knots, reprocessing then providing for determination of knot boundaries.

In the prior art applicant is also aware of U.S. Pat. Nos. 6,272,437 and 6,594,590 which issued on Aug. 7, 2001 and Jul. 15, 2003 respectively to Woods et al. for a Method and Apparatus for Improved Inspection and Classification of Attributes of a Workpiece. Woods et al disclose detecting the probable existence, location and type of defects in a work piece by generating a work piece model based on the signals produced by a sensor subsystem and merging signals from a plurality of such sensor subsystems by the use of a defect assembler. Defects are verified by combining the different results of automatic inspection into a single model.

What is neither taught nor suggested in the prior art, and which is an object of the present invention to provide, is a method and apparatus for determining the displaced size of a knot in a piece of lumber. As known in the prior art, knots typically have a higher density than the surrounding clear wood of the lumber piece, and that the change in density between clear wood and knot may be measured directly using x-ray radiation, that is, by detecting the intensity of x-ray radiation which impinges an x-ray sensor positioned on an opposite side from a radiation source of known intensity.

SUMMARY OF THE INVENTION

The displacement method of measuring knot size in lumber according to the present invention is based on a ratio of the values of measurable qualities of the lumber along the length of, and across the width of the lumber piece being measured. For example, x-ray measurements of the density of the lumber, such as by the method known in the prior art, may be processed to determine a ratio of lumber densities which may, for example, be summed across the width of the lumber piece and in particular across regions of the lumber piece having knots so as to produce a measured knot density profile at that location. The ratio of the measured knot density profile values with the summed values of the maximum knot density found in the lumber piece, wherein both values are adjusted by subtracting from each value the summed measured clear density of the lumber piece, produces a ratio which when multiplied by the measured width of the lumber piece produces the displacement size of the knot. Thus, one object of the present invention is to provide a method and apparatus for defining the size of knot in a lumber piece using x-ray means as better described below.

In summary the method according to one aspect of the present invention may be characterized as a method of estimating the displaced size of a knot in a lumber piece comprising the steps of:

a) providing a radiation source on a first side of a flow path, b) providing a radiation sensor on an opposite second side of the flow path and cooperating with the first radiation source, c) translating the lumber piece downstream along the flow path and between the radiation source and the radiation sensor while simultaneously irradiating the lumber piece with radiation from the radiation source whereby the radiation is attenuated by the lumber piece, d) collecting a set of radiation intensity data from the radiation sensor as the lumber piece is irradiated as it is translated between the radiation source and the radiation sensor, e) processing the set of radiation intensity data to sum the radiation intensity data and to provide radiation intensity profiles transversely of the flow path direction of the flow path and corresponding density profiles transversely of the flow path direction, f) mapping the density profiles to model a set of three dimensional density profiles of the lumber piece, g) processing the radiation intensity data to determine a clear wood density threshold value for the lumber piece and a maximum density value of the density profiles, h) computing a ratio of the summed density profile values to the summed maximum density values for the density profiles and multiplying the ratio with the transverse width of the lumber piece.

The ratio may be advantageously computed according to:

$$\frac{\text{displacement}}{\text{size}} = \frac{\Sigma \text{ measured knot density} - \Sigma \text{ measured clear density}}{\Sigma \text{ max knot density} - \Sigma \text{ measured clear density}}$$

The width may be a measured width.

In alternative embodiments, each radiation sensor may include a plurality of radiation sensors. The radiation sensor and source may be fixed relative to the flow path or may, for example rotate, in oppositely disposed relation, around a track, which may for example be circular, in a plane orthogonal to the flow path.

In a further aspect, the present invention includes a computer program product for use in conjunction with a device having a radiation source on a first side of a flow path and a first radiation sensor on an opposite second side of the flow path and cooperating with the radiation source wherein a lumber piece translates downstream along the flow path and between the radiation source and the radiation sensor while the device simultaneously irradiates the lumber piece with radiation from the radiation source whereby the radiation is attenuated by the lumber piece, wherein the computer program product includes:

a) a computer usable medium having computer readable program code means embodied in the medium for causing the sensing of a lumber piece using the radiation sensor to detect the attenuated radiation and thereby to collect information about the lumber piece;

b) computer readable program code means for causing the collection of a set of radiation intensity data from the radiation sensor as the lumber piece is irradiated as it is translated between the radiation source and the sensor, c) computer readable program code means for causing the processing of the set of radiation intensity data to sum the radiation intensity data and to provide radiation intensity profiles transversely of the flow path direction of the flow path and corresponding density profiles transversely of the flow path direction, d) computer readable program code means for causing the mapping of the density profiles to model a set of three dimensional density profiles of the lumber piece, e) computer readable program code means for causing the processing of the radiation intensity data to determine a clear wood density threshold value for the lumber piece and a maximum density value of the density profiles, f) computer readable program code means for causing the computing of a ratio of the summed density profile values to the summed maximum density values for the density profiles and the multiplication of the ratio with the transverse width of the lumber piece.

In the computer program product the ratio may be described as follows:

$$\text{ratio} = \frac{\Sigma \text{ measured knot density} - \Sigma \text{ measured clear density}}{\Sigma \text{ max knot density} - \Sigma \text{ measured clear density}}$$

DETAILED DESCRIPTION OF EMBODIMENTS OF THE INVENTION

Figure 1:
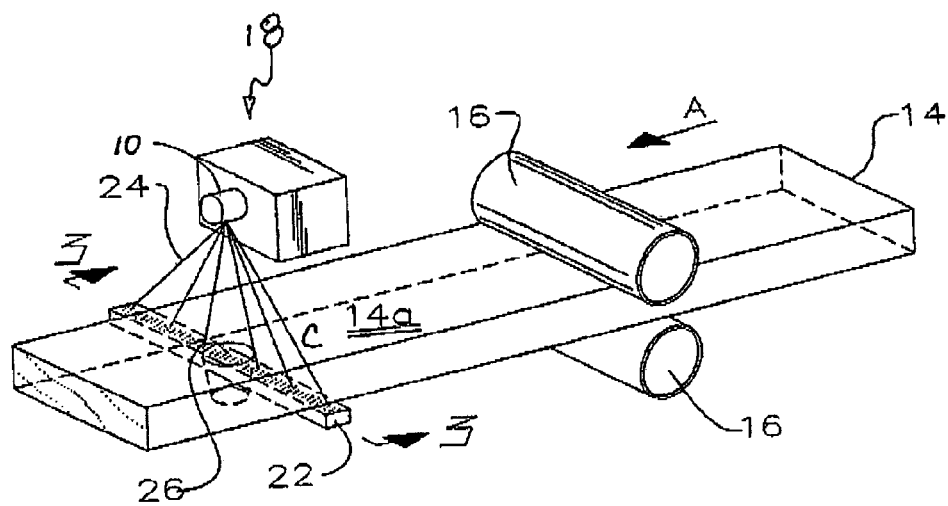
FIG. 1 is, in perspective view, an x-ray source and detector wherein the x-ray source is irradiating a board passing therebetween.
Figure 2:
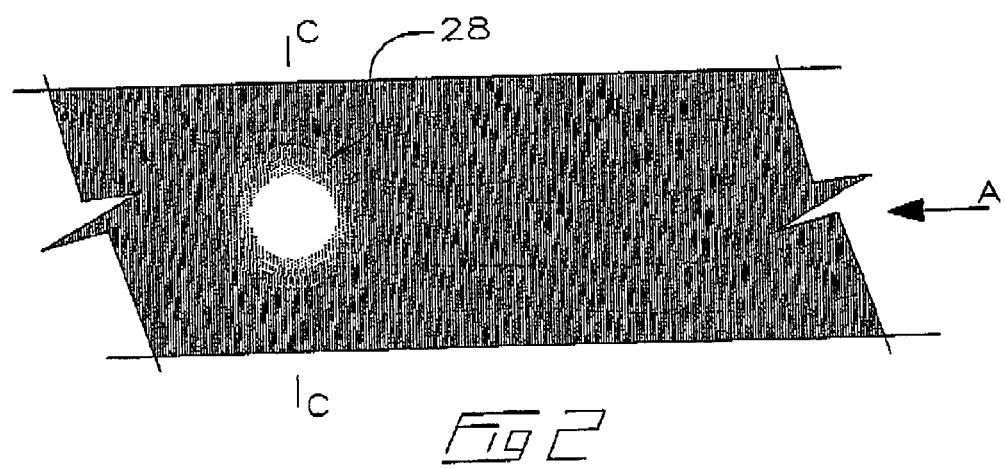
FIG. 2 is, in partially cut away plan view, the board of FIG. 1 showing a knot defect.

As seen in FIG. 1, an x-ray source 10 is irradiating a lumber piece 14 travelling in flow direction A clamped between infeed press rolls 16 on the infeed or upstream side of scanner 18, and exiting from a scanner between outfeed press rolls on the outfeed or downstream side.

The scanner may in one embodiment include x-ray source 10 for example mounted above a lumber piece 14 when lumber piece 14 is passing through the scan plane, in which case an x-ray radiation detector such as a diode detector 22 is mounted underneath lumber piece 14 when passing through the scan plane. X-ray radiation 24 is projected in a radiation plane C generally parallel to the scan plane so as to scan a lateral cross-section or profile across lumber piece 14 as lumber piece 14 is translating in direction A.

As a knot 26 in lumber piece 14 is translated through the radiation plane C of x-ray radiation 24, a "shadow" or attenuated image 28 of knot 26 is detected by detector 22. Knots 26 are often irregular in shape, and of varying shape and size through the thickness of a lumber piece so as to render mere visual estimating of a knot size inaccurate. Thus by way of example in FIGS. 2, 3, 5a and 5b, knot 26 is illustrated as an inverted frusto-conical shape having a diameter "a" adjacent upper surface 14a of lumber piece 14, and a diameter "b" adjacent lower surface 14b of lumber piece 14. Thus the absorption by knot 26 of x-ray radiation 24 is greatest through the core 26a of knot 26, that is, that section corresponding vertically in the illustration to diameter "b". The conical shape of side 26b of knot 26 defines in this example a frusto-conically shaped collar section 26c around core 26a. Attenuated image 28 on detector 22 therefore detects the least amount of x-ray radiation impinging the detector in core shadow 28a, and increasing levels of x-ray radiation impinging the detector increasing radially outwardly in direction D across conical shadow section 28b corresponding to conical section 26c of knot 26.

Figure 3:
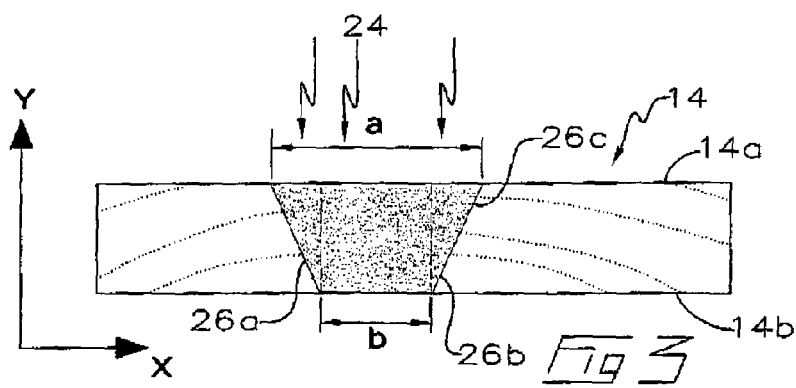
FIG. 3 is, a sectional view, partially cut away, along line 3—3 in FIG. 1.
Figure 4:
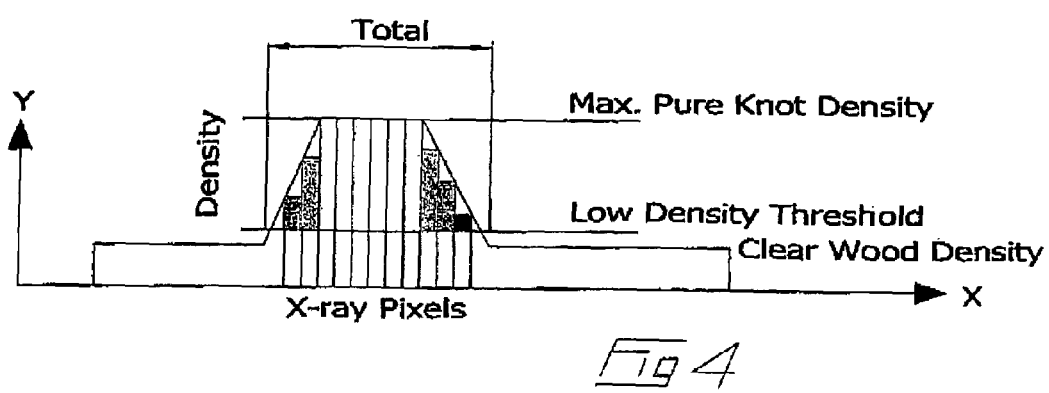
FIG. 4 is a graphical representation of the density of the knot of FIG. 3.
Figure 5A:
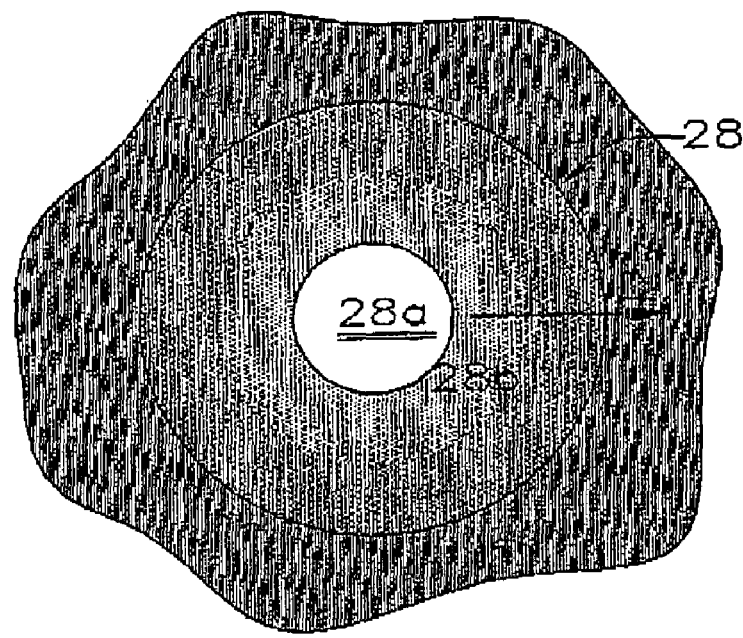
FIG. 5a is, in plan view, is a representation of the radiation intensity detected by the detector once the radiation has been attenuated by the knot of FIG. 3.
Figure 5B:
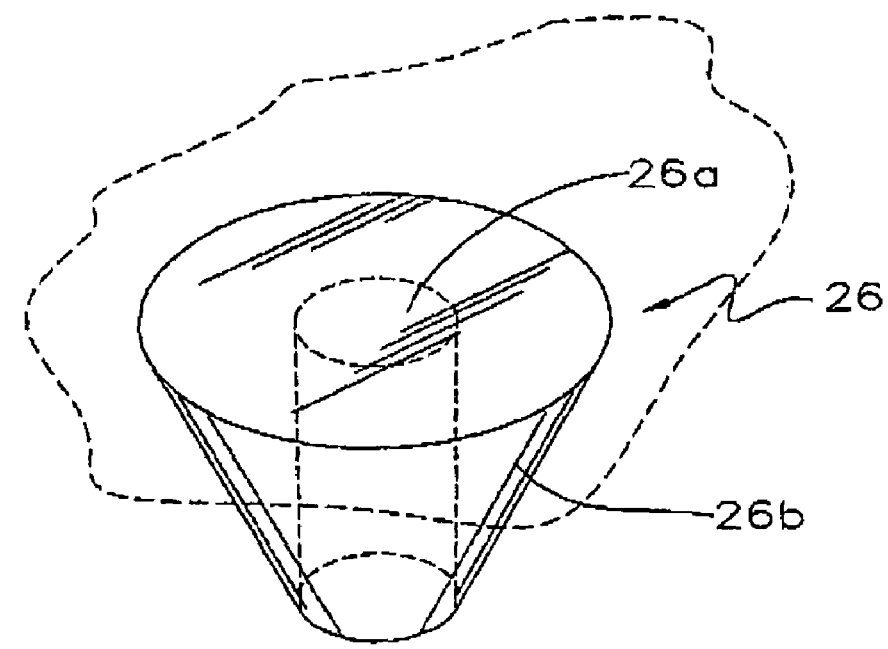
FIG. 5b is, in perspective view, the knot of FIG. 3.

Thus the corresponding graph of FIG. 4, aligned vertically with FIG. 3 to indicate the correspondences between radiation levels land location in the knot, indicates a maximum density corresponding to core 26a and core shadow 28a flanked on either side by radially outwardly decreasing density corresponding to conical section 26c and conical shadow section 28b.

Thus as is presently done manually in the prior art to satisfy lumber grading requirements the average end area of a visually detected knot is multiplied by the board thickness to estimate the knot volume. In the present invention, a radiation source such as an x-ray source which radiation has the characteristic of passing through the board while being detectably attenuated by the presence of differential density such as presented by the presence of a knot, is detected and measured by a corresponding radiation detector as the board is translated between the radiation source and detector. Thus for example if the board is translating in its longitudinal direction at high speed, the radiation source and corresponding detector may, as the board passes through, record density profiles of the board at increments along the board where the spacing between the increments is determined for example by the board translation velocity and the sample rate of the radiation detector. Thus the radiation signal intensity as detected by the detector data is transferred to a processor for each profile and the processor then assembles or processes the signal intensity data for each profile into corresponding density profiles so as to model the density of the board along its length, wherein the density is inversely proportional to the signal intensity of the detected radiation. Thus as described above, the detector receives a shadow image of both the clear wood of the board and the knots found in the board whether or not they may be seen visibly on the sides or edges of the board. The shadow image, being the analogy given the attenuated radiation signal intensity as detected by the detector as the signal intensity changes due to the change in density within the board caused by the presence of a knot, provides then for easily visualized examples such as illustrated wherein the most dense material is a white area surrounded by a grey area graduating from white to dark grey at the edge of the knot where the dense material is thinnest. The shadow image then transitions into the grey color representing the clear wood density. Where knots are segmented, this information may be extracted from the shadow image data. Similarly other challenges to the accurate sizing of knots may be assessed by analysing the shadow image data for example so as to detect pitch streaks, compression wood, knot clusters and their separation. Thus in analysing the shadow images the detected knot areas may be mapped or "grown" to correspond to the internal size and outwardly visually undetectable knot volume internal to the board and to remove shadow image information merely corresponding to pitch areas.

Thus returning to FIG. 4, the knot size or volume is shown graphically as the sum of the densities across the width of the board, divided by the theoretical maximum density of the board material, that ratio then multiplied by the board width. In then processing that information it is necessary to determine the theoretical maximum density of the board and compare the measured board density to that theoretical maximum density. If the theoretical maximum density is met or exceeded by a measured density, then it may be assumed that the knot fully penetrates the board thus corresponding to the weakest radiation signal intensity, that is, the area where the radiation is most attenuated, as detected by the radiation detector. If the theoretical maximum density is not met, then there is less than full penetration of the board by the knot resulting in a graduated, that is lighter to darker shadow image keeping in mind that although the illustrated example is of a relatively simple knot structure. In reality knots will not necessarily be simply mathematically described shapes but will be of a variety of shapes and inclination and thicknesses and may or may not be wholly or partially visible on any exterior surface of the board.

Figure 6:
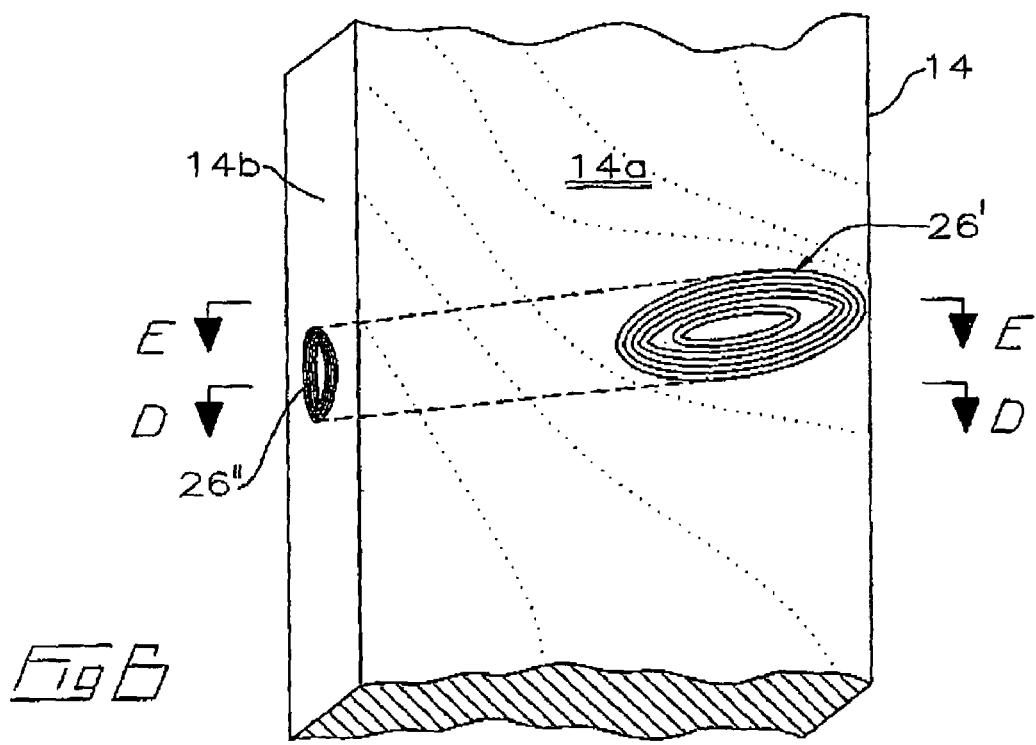
FIG. 6 is, in perspective partially cut away view, a board segment illustrating a knot which extends inclined non-orthogonally through the board.
Figure 7:
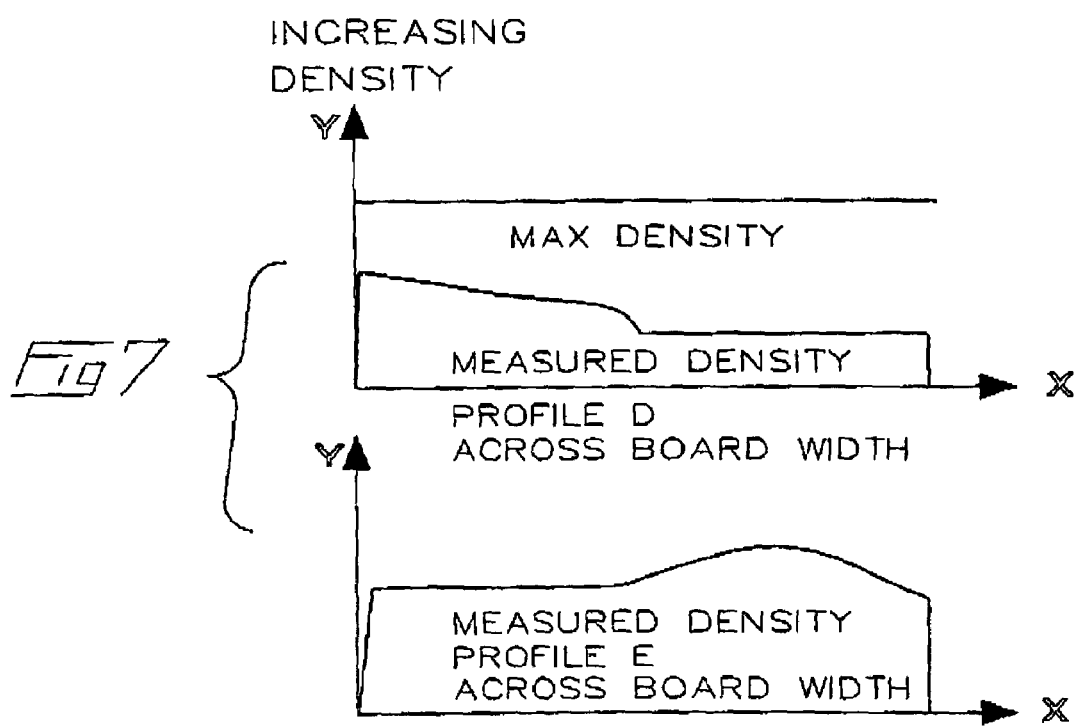
FIG. 7 is a graphical representation of the density profile of the board of FIG. 6 along lines D—D and E—E respectively.

As seen in FIG. 6, a knot 26' in a board 14 is often not symmetric about an axis of symmetry perpendicular to the board such as in the example of FIGS. 1–5, but may instead be slanted through the board so that its long axis is not orthogonal to any face of the board and extends partially submerged through the board. In many instances the knot will appear visually on one or more faces of the board so that for example knot 26' appears as a large elliptical knot on upper surface 14a of the board and as a smaller elliptical knot 26" on edge surface 14b. Thus the density profile shown by way of example as density profiles D taken along line D—D and density profile E taken along E—E would be modelled according to the method described above in respect of knot 26, but additional visual information as to the size and position of knots 26' and 26" assists in the method according to the present invention. In particular, in one embodiment, the scanner includes a vision system which includes a light source such as a laser and a camera for detecting visible defects on all surfaces of board 14. Thus by way of example, a light source may illuminate a surface of board 14 and the reflection captured by a corresponding light detector as now well known in the art. The results in scanning of profiles of board 14 as board 14 translates through such a machine results in the detecting of contrast between the lighter surface of the clear wood of board 14 and the darker surface of knots 26' and 26". This contrast data is then processed in the processor to merge the contrast data with the density data based model according to the present invention so as to improve the model of the knot and thereby allow improved board intensity determination.

Figure 8:
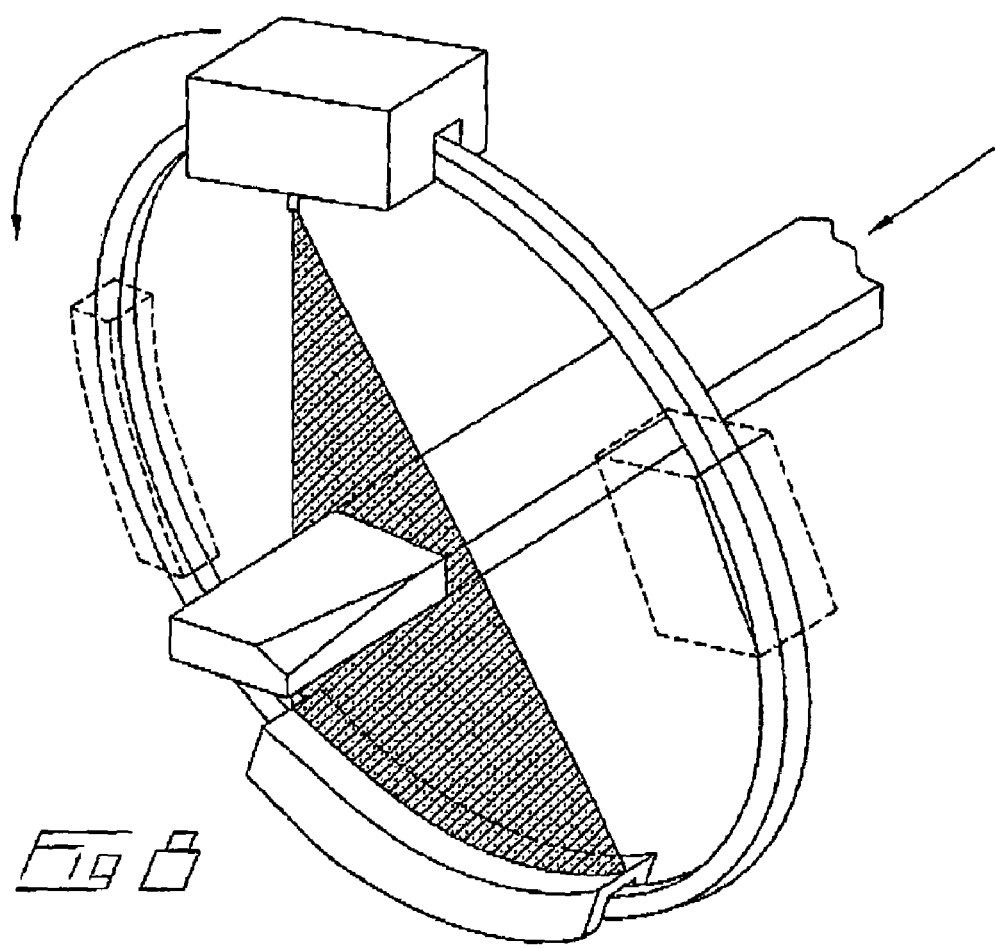
FIG. 8 is, in perpendicular view, an embodiment wherein the radiation source and detector rotate three hundred sixty degrees about the workpiece.

In a further embodiment of FIG. 8, the radiation source, which may without intending to be limiting be an x-ray radiation source, rotates three hundred sixty degrees around the board as the board translates along its flow path. A corresponding radiation detector, oppositely disposed to the radiation source, also rotates simultaneously three hundred sixty degrees around the board so as to remain exposed to the attenuated radiation passing through the board from the radiation source. More than one source/detector pair may be employed. The source/detector pairs may rotate around a path, which may be planar, which is circular or otherwise symmetric about the flow path or long axis of the board.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A method of estimating the displaced size of a knot in a lumber piece comprising the steps of:
   a) providing a first radiation source on a first side of a flow path;

b) providing a first radiation sensor on an opposite second side of said flow path and cooperating with said first radiation source;

c) translating the lumber piece downstream along said flow path and between said first radiation source and said first radiation sensor while simultaneously irradiating the lumber piece with radiation from said first radiation source whereby said radiation is attenuated by said lumber piece;

d) collecting a set of first radiation intensity data from said first radiation sensor as the lumber piece is irradiated as it is translated between said first radiation source and said first sensor;

e) processing said set of first radiation intensity data to sum said first radiation intensity data and to provide radiation intensity profiles transversely of the flow path direction of said flow path and corresponding density profiles transversely of said flow path direction;

f) mapping said density profiles to model a first set of three dimensional density profiles of the lumber piece;

g) processing said first radiation intensity data to determine a clear wood density threshold value for the lumber piece and a maximum density value of said density profiles; and h) computing a ratio of the summed density profile values to the summed maximum density values for said density profiles and multiplying said ratio with the transverse width of the lumber piece.

2. A method as defined in claim 1 wherein said ratio is computed according to:

$$\text{ratio} = \frac{\Sigma \text{ measured knot density} - \Sigma \text{ measured clear density}}{\Sigma \text{ max knot density} - \Sigma \text{ measured clear density}}$$

and wherein said width is a measured width.

3. A method as defined in claim 2 wherein said first radiation sensor comprises a plurality of radiation sensors.

4. A computer program product for use with a device having a first radiation source on a first side of a flow path and a first radiation sensor on an opposite second side of said flow path and cooperating with said first radiation source wherein a lumber piece translates downstream along said flow path and between said first radiation source and said first radiation sensor while said device simultaneously irradiates the lumber piece with radiation from said first radiation source whereby said radiation is attenuated by said lumber piece, said computer program product comprising:

a) a computer usable medium having computer readable program code means embodied in said medium for causing the sensing of a lumber piece using said first radiation sensor to detect the attenuated radiation and thereby to collect information about the lumber piece;

b) computer readable program code means for causing the collection of a set of first radiation intensity data from said first radiation sensor as the lumber piece is irradiated as it is translated between said first radiation source and said first sensor;

c) computer readable program code means for causing the processing of said set of first radiation intensity data to sum said first radiation intensity data and to provide radiation intensity profiles transversely of the flow path direction of said flow path and corresponding density profiles transversely of said flow path direction;

d) computer readable program code means for causing the mapping of said density profiles to model a first set of three dimensional density profiles of the lumber piece;

e) computer readable program code means for causing the processing of said first radiation intensity data to determine a clear wood density threshold value for the lumber piece and a maximum density value of said density profiles; and f) computer readable program code means for causing the computing of a ratio of the summed density profile values to the summed maximum density values for said density profiles and the multiplication of the ratio with the transverse width of the lumber piece.

5. The computer program product of claim 4 wherein said ratio is $$\text{ratio} = \frac{\Sigma \text{ measured knot density} - \Sigma \text{ measured clear density}}{\Sigma \text{ max knot density} - \Sigma \text{ measured clear density}}.$$

6. The computer program product of claim 5 for use with a device having a second radiation source cooperating with a second radiation sensor, wherein the device simultaneously irradiates said lumber piece during said translation along said flow path with radiation from said second radiation source, said computer program product further comprising:

a) computer readable program code means for causing the collection of a set of second radiation intensity data from said second radiation sensor as said lumber piece is irradiated during said translation; and b) computer readable program code means for causing the processing of said second radiation intensity data together with said first set of three dimensional density profiles to provide a second set of three dimensional density profiles of said lumber piece merging said first and second sets.

7. The computer program product of claim 6 wherein said first radiation sensor comprises a plurality of radiation sensors.

8. The computer program product of claim 6 wherein said second radiation sensor comprises a plurality of radiation sensors.

* * * * *